United States Patent
Taracila et al.

(10) Patent No.: US 11,360,168 B2
(45) Date of Patent: Jun. 14, 2022

(54) SYSTEMS AND METHODS FOR A NECK RADIO FREQUENCY COIL FOR MR IMAGING

(71) Applicant: General Electric Company, Schenectady, NY (US)

(72) Inventors: Victor Taracila, Beachwood, OH (US); Balint Franko, Streetsboro, OH (US); Mark Giancola, Chesterland, OH (US); Yun-Jeong Stickle, Solon, OH (US); Clyve Konrad Rosales Follante, Twinsburg, OH (US); Fraser John Laing Robb, Aurora, OH (US)

(73) Assignee: General Electric Company, Schenectady, NY (US)

( * ) Notice: Subject to any disclaimer, the term of this patent is extended or adjusted under 35 U.S.C. 154(b) by 400 days.

(21) Appl. No.: 16/198,713

(22) Filed: Nov. 21, 2018

(65) Prior Publication Data
US 2020/0158800 A1    May 21, 2020

(51) Int. Cl.
*G01R 33/34* (2006.01)
*G01R 33/3415* (2006.01)
(Continued)

(52) U.S. Cl.
CPC ........ *G01R 33/34084* (2013.01); *A61B 5/055* (2013.01); *A61B 5/6822* (2013.01); *A61G 13/121* (2013.01); *G01R 33/3415* (2013.01)

(58) Field of Classification Search
CPC .......... G01R 33/34084; G01R 33/3415; G01R 33/3628; G01R 33/34; G01R 33/34046; A61B 5/055; A61B 5/6822; A61G 13/121
See application file for complete search history.

(56) References Cited

U.S. PATENT DOCUMENTS

| 4,621,237 A | 11/1986 | Timms |
| 6,980,000 B2 * | 12/2005 | Wong ............... G01R 33/34053 324/318 |

(Continued)

FOREIGN PATENT DOCUMENTS

| WO | 2018098331 A1 | 5/2018 |
| WO | 2018098355 A1 | 5/2018 |

OTHER PUBLICATIONS

European application No. 19210485.9 filed Nov. 20, 2019—European extended Search Report dated Aug. 10, 2020; 15 pages.

(Continued)

*Primary Examiner* — Catherine B Kuhlman
*Assistant Examiner* — Nicholas A Robinson

(57) ABSTRACT

Various systems are provided for neck radio frequency (RF) coil assemblies for a magnetic resonance imaging (MRI) system. In one example, a neck RF coil assembly includes a central RF coil array including a first plurality of RF coils configured to cover a neck of a subject to be imaged, an upper RF coil array including a second plurality of RF coils extending upward from the central RF coil array and configured to cover a lower head region of the subject, and a lower RF coil array including a third plurality of RF coils extending downward from the central RF coil array and configured to cover an upper shoulder region of the subject, wherein each RF coil of the first, second, and third pluralities of RF coils comprises a loop portion comprising two distributed capacitance wire conductors encapsulated and separated by a dielectric material.

11 Claims, 8 Drawing Sheets

(51) Int. Cl.
  *A61B 5/055*  (2006.01)
  *A61B 5/00*  (2006.01)
  *A61G 13/12*  (2006.01)

(56) References Cited

U.S. PATENT DOCUMENTS

| | | |
|---|---|---|
| 7,333,849 B1 | 2/2008 | Su et al. |
| 7,663,367 B2 | 2/2010 | Wiggins |
| 9,002,431 B2 | 4/2015 | Jones |
| 9,568,572 B2 * | 2/2017 | Vaughan ............ G01R 33/3692 |
| 2005/0107686 A1 * | 5/2005 | Chan .................. G01R 33/3415 |
| | | 600/422 |
| 2008/0100294 A1 * | 5/2008 | Rohling ........... G01R 33/34084 |
| | | 324/318 |
| 2008/0204021 A1 * | 8/2008 | Leussler ............ G01R 33/3415 |
| | | 324/318 |
| 2014/0210466 A1 | 7/2014 | Arias et al. |
| 2015/0017378 A1 | 1/2015 | Stone |
| 2016/0356867 A1 | 12/2016 | Fujita |
| 2018/0263561 A1 * | 9/2018 | Jones ............... G01R 33/34007 |
| 2018/0335491 A1 * | 11/2018 | Yang .................... G01R 33/341 |

OTHER PUBLICATIONS

CN application 201911101528.7 filed Nov. 12, 2019—first Office Action dated Oct. 11, 2021; 10 pages.

* cited by examiner

SYSTEMS AND METHODS FOR A NECK RADIO FREQUENCY COIL FOR MR IMAGING

FIELD

Embodiments of the subject matter disclosed herein relate to magnetic resonance imaging (MM), and more particularly, to MM radio frequency (RF) coils.

BACKGROUND

Magnetic resonance imaging (MRI) is a medical imaging modality that can create images of the inside of a human body without using x-rays or other ionizing radiation. MM systems include a superconducting magnet to create a strong, uniform, static magnetic field $B_0$. When a human body, or part of a human body, is placed in the magnetic field $B_0$, the nuclear spins associated with the hydrogen nuclei in tissue water become polarized, wherein the magnetic moments associated with these spins become preferentially aligned along the direction of the magnetic field $B_0$, resulting in a small net tissue magnetization along that axis. MRI systems also include gradient coils that produce smaller amplitude, spatially-varying magnetic fields with orthogonal axes to spatially encode the magnetic resonance (MR) signal by creating a signature resonance frequency at each location in the body. The hydrogen nuclei are excited by a radio frequency signal at or near the resonance frequency of the hydrogen nuclei, which add energy to the nuclear spin system. As the nuclear spins relax back to their rest energy state, they release the absorbed energy in the form of an RF signal. This RF signal (or MR signal) is detected by one or more RF coils and is transformed into the image using reconstruction algorithms.

BRIEF DESCRIPTION

In one embodiment, an RF coil assembly for an MM system includes a central RF coil array including a first plurality of RF coils configured to cover a neck of a subject to be imaged, an upper RF coil array including a second plurality of RF coils extending upward from the central RF coil array and configured to cover a lower head region of the subject, and a lower RF coil array including a third plurality of RF coils extending downward from the central RF coil array and configured to cover an upper shoulder region of the subject, wherein each RF coil of the first, second, and third pluralities of RF coils comprises a loop portion comprising two distributed capacitance wire conductors encapsulated and separated by a dielectric material.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 2:
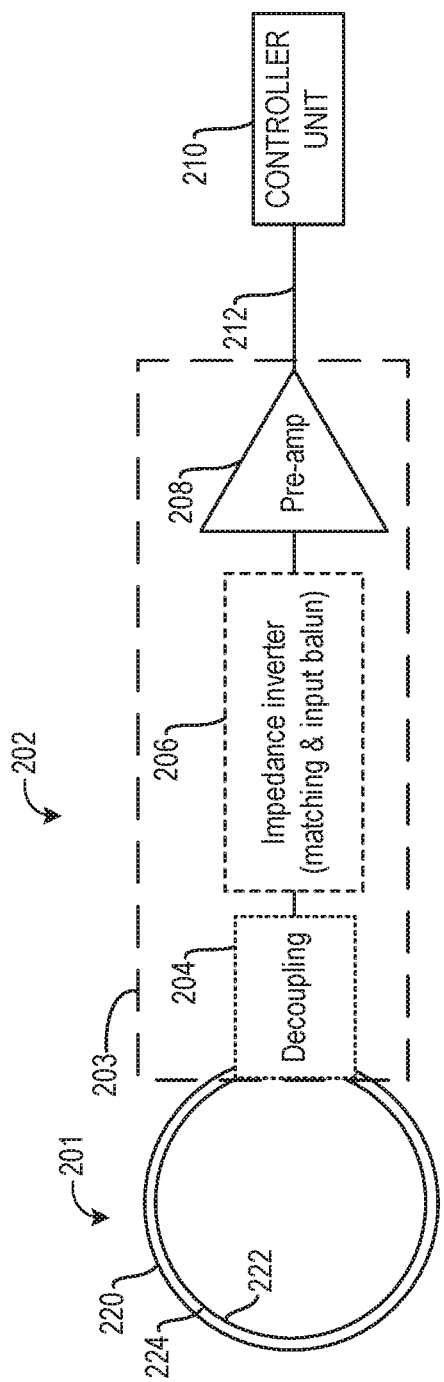
FIG. 2 schematically shows an example RF coil coupled to a controller unit.
Figure 3:
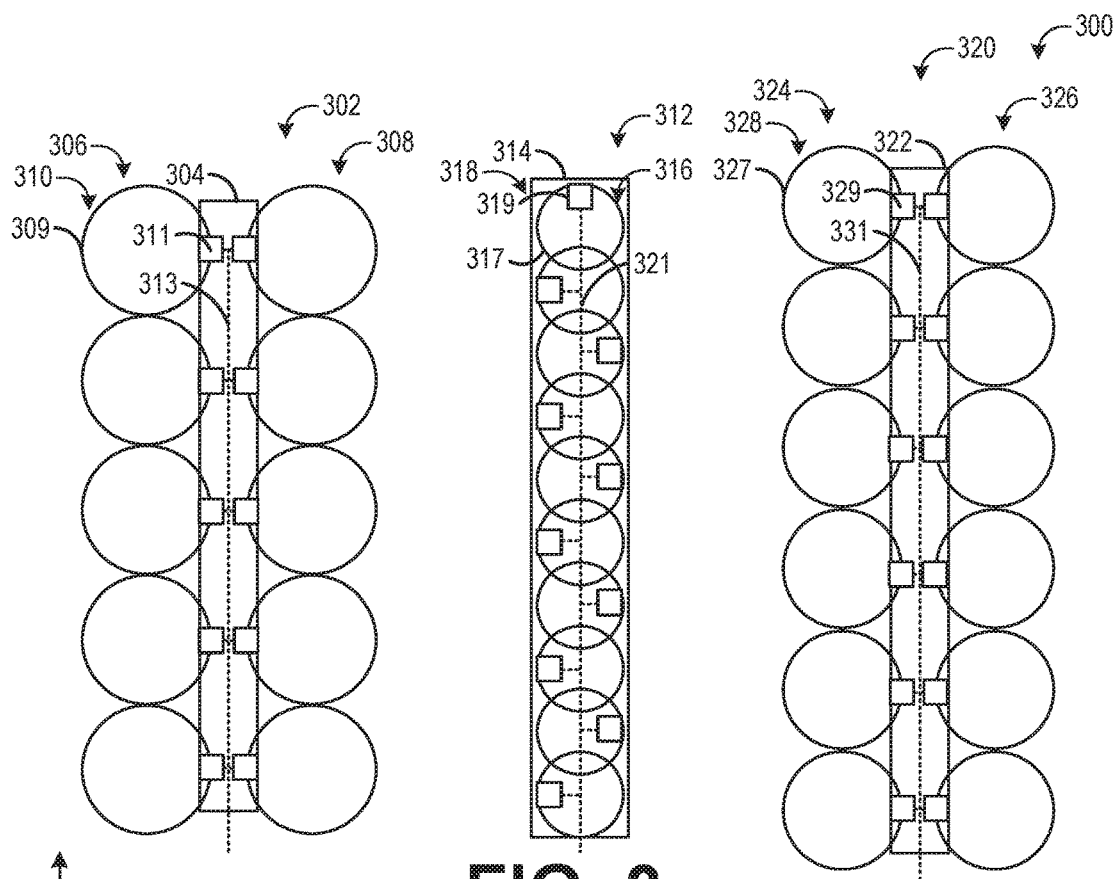
FIG. 3 schematically shows a plurality of RF coil arrays that may be assembled to form a first example RF coil assembly.
Figure 7:
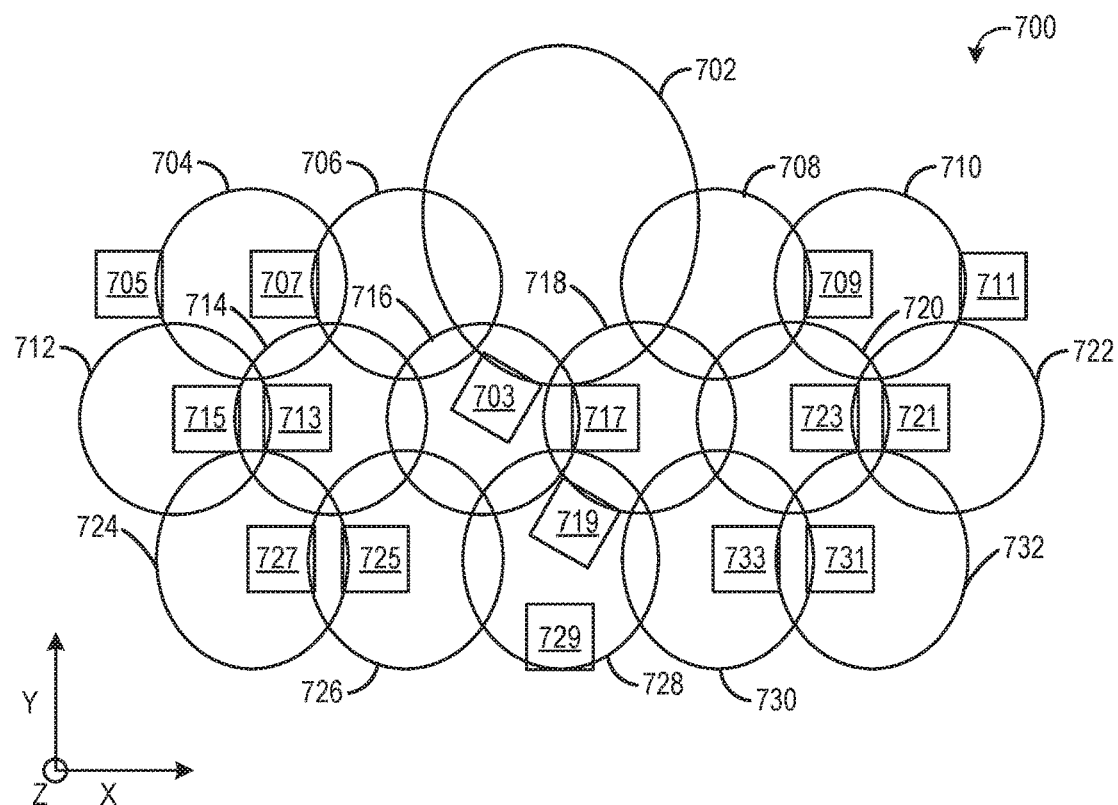
FIG. 7 schematically shows an RF coil array including RF coil loops and coupling electronics that may be included as part of a second example RF coil assembly.

The following description relates to various embodiments of a radio frequency (RF) coil assembly for an MRI system. An MM system, such as the MM system shown by FIG. 1, includes a receive RF coil unit that may be comprised of one or more RF coils. For example, the receive RF coil unit may comprise an array of RF coils, as shown in FIGS. 3 and 7. The RF coils are configured with coupling electronics and distributed capacitance wire conductors, as shown in FIG. 2, such that each RF coil is lightweight, flexible, and transparent to each other RF coil. In this way, the RF coils may be positioned against a body of a patient and wrapped around the patient in order to image portions of the body that include complicated geometries. Because the RF coils include the coupling electronics and distributed capacitance wire conductors, the RF coils may move and/or overlap relative to each other without degradation of MR signals transmitted to the MRI system by the RF coils.

The receive RF coil unit may be used to image a head, neck, chest, and/or spine region of a patient. However, different patients may have different sized necks, as the neck region exhibits large variation in size across various patient populations. Further, the neck includes complicated geometry (such as a relatively narrow middle portion of the neck flaring upward and outward toward the jaw and also flaring downward and outward toward the chest). This variability in the neck anatomy from patient to patient and also the complicated geometry of the neck results in receive RF coil units that may not conform sufficiently to the patient anatomy to adequately image all areas of the anatomy, such as the cervical spine. Further, when typical RF coil units are made to conform tightly to the patient anatomy, the patient may experience discomfort due to the close proximity of the RF coil unit, which may be comprised of rigid and/or waterproof material that may be uncomfortable when placed tightly around the patient's neck, chest, head, and spine region.

Thus, according to embodiments disclosed herein, a neck RF coil assembly may be configured to tightly conform to the patient anatomy without causing undue discomfort to the patient. The neck RF coil assembly may include a plurality of RF coils as described above and shown in FIG. 2. Owing to the lightweight and flexible nature of the conductors and small coupling electronics of the RF coils, the RF coils may be mounted on lightweight and flexible material that may conform tightly to patient anatomy and accommodate a variety of different patient sizes.

For example, a first neck RF coil assembly, as shown in FIGS. 3-6, may include three RF coil arrays that are stacked upon each other to form a collar-like structure with a central RF coil array that is configured to wrap around the narrow (e.g., middle) part of a neck of a subject and two peripheral RF coil arrays that, when stacked upon each other and the central RF coil array, form two rows of staggered RF coils. When the first neck RF coil assembly is worn by a subject, one of the two rows of staggered RF coils flares upward and outward from the center to surround a jaw/lower face of the subject and the other of the two rows of staggered RF coils flares downward and outward from the center to surround an upper chest/shoulders of the subject. The RF coils that form the two peripheral RF coil arrays may be attached to a respective substrate in an open loop manner, such that only a relatively small portion of each RF coil is attached to the substrate and the remaining portion of each RF coil is "open" to the environment. This open loop arrangement may allow the RF coils forming the two peripheral RF coil arrays to bend, flex, and otherwise move free from any restrictions that typical substrate/enclosure configurations may impose, thereby allowing the RF coils to conform around the complex geometry of the head, neck, and spine region.

A second neck RF coil assembly, as shown in FIGS. 7-13, may include a semi-rigid substrate shaped to fit over a chest and anterior neck/jaw region of a subject. The substrate may include flaps configured to extend from the subject's cheeks back along the sides of the neck, under the subject's ears, akin to a reverse neck pillow. In some examples, the substrate may include a chin strap configured to cover a chin of the patient. A plurality of RF coils are coupled to inner surfaces the substrate. The substrate may be comprised of foam or other semi-rigid material and various joints, hinges, or flex regions of the second neck RF coil assembly may be provided via the foam substrate rather than traditional coupling/hinging mechanisms. When the second neck RF coil assembly is worn by a patient, the RF coils coupled to the substrate may be brought in close proximity to the chest, anterior neck and chin, and the sides/back of the neck, thereby facilitating high quality imaging of all areas of the neck/spine region.

Figure 1:
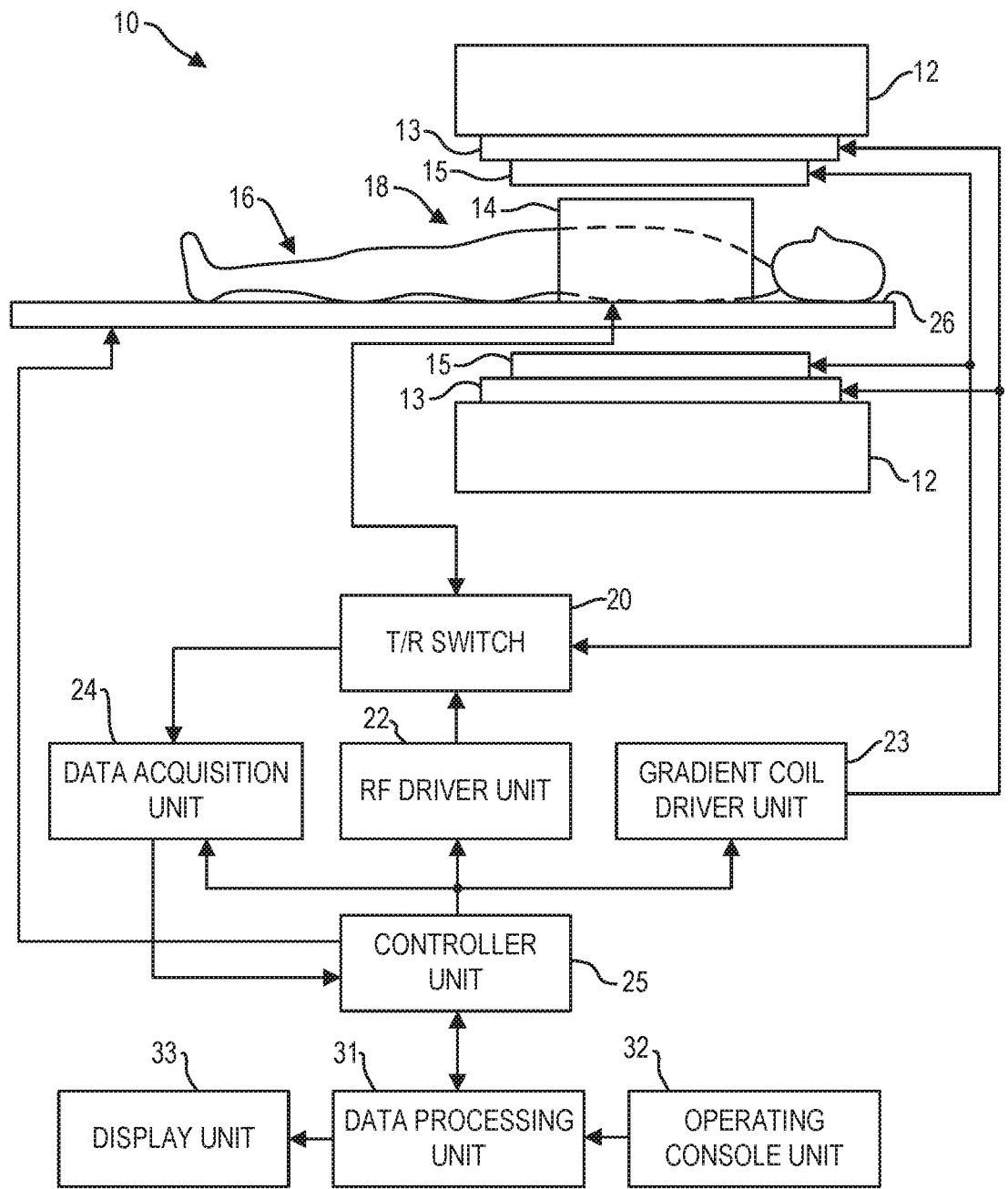
FIG. 1 is a block diagram of an Mill system according to an exemplary embodiment.

FIG. 1 illustrates a magnetic resonance imaging (MM) apparatus 10 that includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, a data processing unit 31, an operating console unit 32, and a display unit 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI apparatus 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MM apparatus 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MM apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a two-dimensional (2D) slice image or three-dimensional (3D) image of the subject 16 generated by the data processing unit 31.

During a scan, RF coil array interfacing cables (not shown in FIG. 1) may be used to transmit signals between the RF coils (e.g., RF coil unit 14 and RF body coil unit 15) and other aspects of the processing system (e.g., data acquisition unit 24, controller unit 25, and so on), for example to control the RF coils and/or to receive information from the RF coils. As explained previously, the RF body coil unit 15 is a transmit coil that transmits RF signals, and the local surface RF coil unit 14 receives the MR signals. More generally, RF coils are used to transmit RF excitation signals ("transmit coil"), and to receive the MR signals emitted by an imaging subject ("receive coil"). In some embodiments, the transmit and receive coils are a single mechanical and electrical structure or array of structures, with transmit/receive mode switchable by auxiliary circuitry. In other examples, the transmit body coil (e.g., RF body coil unit 15) and the surface receive coil (e.g., RF coil unit 14) may be separate components. For enhanced image quality, however, it may be desirable to provide a receive coil that is mechanically and electrically isolated from the transmit coil. In such case it is desirable that the receive coil, in its receive mode, be electromagnetically coupled to and resonant with an RF "echo" that is stimulated by the transmit coil. However, during transmit mode, it may be desirable that the receive coil is electromagnetically decoupled from and therefore not resonant with the transmit coil, during actual transmission of the RF signal. Such decoupling averts a potential problem of noise produced within the auxiliary circuitry when the receive coil couples to the full power of the RF signal.

Additional details regarding the uncoupling of the receive RF coil will be described below.

Turning now to FIG. 2, a schematic view of an RF coil 202 coupled to a controller unit 210 is shown according to an exemplary embodiment. The RF coil 202 includes a loop portion 201 and a coupling electronics portion 203 which is coupled to the controller unit 210 via a coil-interfacing cable 212. In some embodiments, the RF coil may be a surface receive coil, which may be single- or multi-channel. The RF coil 202 may be used in RF coil unit 14 of FIG. 1 and as such may operate at one or more frequencies in the MIll apparatus 10. The coil-interfacing cable 212 may extend between the electronics portion 203 and an interfacing connector of an RF coil array and/or between the interfacing connector of the RF coil array and the MM system controller unit 210. The controller unit 210 may correspond to and/or be associated with the data processing unit 31 and/or controller unit 25 in FIG. 1.

The loop portion 201 may be comprised of at least two parallel conductors that form a distributed capacitance along the length of the loop portion. In the example shown in FIG. 2, the loop portion 201 includes a first conductor 220 and a second conductor 222 which exhibit a substantially uniform capacitance along the entire length of the loop portion. Distributed capacitance (DCAP), as used herein, represents a capacitance exhibited between conductors that distributes along the length of the conductors and may be void of discrete or lumped capacitive components and discrete or lumped inductive components. The DCAP can also be called incorporated capacitance. In some embodiments, the capacitance may distribute in a uniform manner along the length of the conductors.

A dielectric material 224 encapsulates and separates the first and second conductors 220, 222. The dielectric material 224 may be selected to achieve a desired distributive capacitance. For example, the dielectric material 224 may be selected based on a desired permittivity E. In particular, the dielectric material 224 may be air, rubber, plastic, or any other appropriate dielectric material. In some embodiments, the dielectric material may be polytetrafluoroethylene (pTFE). The dielectric material 224 may surround the parallel conductive elements of the first and second conductors 220, 222. Alternatively, the first and second conductors 220, 222 may be twisted upon one another to from a twisted pair cable. As another example, the dielectric material 224 may be a plastic material. The first and second conductors 220, 222 may form a coaxial structure in which the plastic dielectric material 224 separates the first and second conductors. As another example, the first and second conductors may be configured as planar strips.

The coupling electronics portion 203 is connected to the loop portion 201 of the RF coil 202. Herein, the coupling electronics portion 203 may include a decoupling circuit 204, impedance inverter circuit 206, and a pre-amplifier 208. The decoupling circuit 204 may effectively decouple the RF coil during a transmit operation. Typically, the RF coil 202 in its receive mode may receive MR signals from a body of a subject being imaged by the MR apparatus. If the RF coil 202 is not used for transmission, then it may be decoupled from the RF body coil while the RF body coil is transmitting the RF signal.

The impedance inverter circuit 206 may include an impedance matching network between the loop portion 201 and the pre-amplifier 208. The impedance inverter circuit 206 is configured to transform an impedance of the loop portion 201 into an optimal source impedance for the pre-amplifier 208. The impedance inverter circuit 206 may include an impedance matching network and an input balun. The pre-amplifier 208 receives MR signals from the loop portion 201 and amplifies the received MR signals. In one example, the pre-amplifier 208 may have a low input impedance configured to accommodate a relatively high blocking or source impedance. The coupling electronics portion 203 may be packaged in a very small PCB, e.g., approximately 2 cm$^2$ in size or smaller. The PCB may be protected with a conformal coating or an encapsulating resin.

The coil-interfacing cable 212, such as a RF coil array interfacing cable, may be used to transmit signals between the RF coils and other aspects of the processing system. The RF coil array interfacing cable may be disposed within the bore or imaging space of the MRI apparatus (such as MM apparatus 10 of FIG. 1) and subjected to electro-magnetic fields produced and used by the MM apparatus. In MM systems, coil-interfacing cables, such as coil-interfacing cable 212, may support transmitter-driven common-mode currents, which may in turn create field distortions and/or unpredictable heating of components. Typically, common-mode currents are blocked by using baluns. Baluns or common-mode traps provide high common-mode impedances, which in turn reduces the effect of transmitter-driven currents. Thus, coil-interfacing cable 212 may include one or more baluns. In some embodiments, the one or more baluns may be continuous baluns, such as distributed, flutter, and/or butterfly baluns. The cable 212 may be a 3-conductor triaxial cable having a center conductor, an inner shield, and an outer shield. In some embodiments, the center conductor is connected to the RF signal and pre-amp control (RF), the inner shield is connected to ground (GND), and the outer shield is connected to the multi-control bias (diode decoupling control) (MC_BIAS).

The RF coil presented above with respect to FIGS. 2 and 3 may be utilized in order to receive MR signals during an MR imaging session. As such, the RF coil of FIG. 2 may be used in RF coil unit 14 of FIG. 1 and may be coupled to a downstream component of the MRI system, such as the controller unit 25. The RF coil may be placed in the bore of the MRI system in order to receive the MR signals during the imaging session, and thus may be in proximity to the transmit RF coil (e.g., the body RF coil unit 15 of FIG. 1). The controller unit may store instructions in non-transitory memory that are executable to generate an image from an imaging subject positioned in the bore of the MRI system during an MR imaging session. To generate the image, the controller unit may store instructions to perform a transmit phase of the MR imaging session. During the transmit phase, the controller unit may command (e.g., send signals) to activate the transmit RF coil(s) in order to transmit one or more RF pulses. To prevent interference leading to $B_1$ field distortion during the transmit phase, the receive RF coil(s) may be decoupled during the transmit phase. The controller unit may store instructions executable to perform a subsequent receive phase of the MR imaging session. During the receive phase, the controller unit may obtain MR signals from the receive RF coil(s). The MR signals are usable to reconstruct the image of the imaging subject positioned in the bore of the MRI system.

Figure 4:
FIG. 4 schematically shows the first example RF coil assembly in an assembled state.

FIG. 3 schematically shows a dissembled view 300 of a neck RF coil assembly comprising three separate RF coil arrays in accordance with a first exemplary embodiment. In the dissembled view 300, the three RF coil arrays are shown separately and are not overlapped with each other. The RF coil assembly includes two peripheral RF coil arrays and a central RF coil array, each comprising a plurality of RF coils similar to the RF coil 202 described above with respect to FIG. 2. Each RF coil array includes a substrate to which the RF coils are attached. When the substrates of each of the RF coil arrays are stacked upon each other, an assembled neck RF coil assembly 400 is formed, as shown in FIG. 4.

The central RF coil array 312 includes a plurality of RF coils 316 distributed in a partially-overlapping manner along a central longitudinal axis of a first substrate layer 314. For example, the plurality of RF coils 316 includes a first RF coil 318. The first RF coil 318 is a non-limiting example of the RF coil 202 illustrated in FIG. 2 and described above, and includes a loop portion 317 (e.g., comprised of least two parallel, distributed capacitance wire conductors encapsulated and separated by a dielectric material) and a coupling electronics portion 319. The coupling electronics portion 319 may include a pre-amplifier, a decoupling circuit, and an impedance inverter circuit, as described above. Each RF coil of the plurality of RF coils 316 may be configured similarly to first RF coil 318, e.g., comprised of a loop portion and coupling electronics portion. As shown, the plurality of RF coils 316 includes ten RF coils, but other configurations are possible, such as eight RF coils. Each loop portion of each RF coil may have the same diameter. In an example, each diameter may be 6 cm. The loop portions may partially overlap along the first substrate layer 314. For example, a bottom segment of the first RF coil 318 (such as the bottom 10% of the loop portion 317) may overlap with a top segment of the RF coil positioned adjacent to the first RF coil 318 (e.g., the loop portion 317 may overlap the top 10% of the loop portion of the RF coil positioned adjacent to the first RF coil). Each RF coil may overlap with neighboring RF coils of the plurality of RF coils 316 by an equal amount. In this way, the RF coils may be distributed equally along the length of the first substrate layer 314 in an overlapping manner.

Each RF coil of the plurality of RF coils 316 fully overlaps with the first substrate layer 314. For example, the first substrate layer 314 may have a width that is wider than the diameter of the RF coils and a length that is longer than a total length of the plurality of RF coils 316 (when the RF coils are distributed as described above). Further, each loop portion of each RF coil may at least partially contact the first substrate layer 314 along the circumference of the loop portion. Each RF coil may be coupled to the first substrate layer in a suitable manner, such as via stitching. While only one first substrate layer 314 is shown (e.g., underneath the plurality of RF coils 316), in some examples, central RF coil array 312 may include a second sheet or layer of substrate (e.g., positioned on top of the plurality of RF coils 316). Further, while FIG. 3 shows the loop portions and coupling electronics portions being coupled to the same side of the first substrate layer 314, in some examples, the coupling electronics portions may be coupled to an opposite side of the first substrate layer 314, and the substrate layer may include holes through which each loop portion may extend in order to facilitate the loop portions being coupled to the respective electronics portions.

Additionally, a coil-interfacing cable 321 extends between each coupling electronics portion and an RF coil interfacing connector. Each of the electrical wires coupled to the coupling electronics portions may be housed together (e.g., bundled together) within the coil-interfacing cable 321 and electrically coupled to the connector. The connector may interface with the MM system (e.g., electrically couple with the MRI system by plugging into an input of the MM system) in order to output signals from the RF coils to the MM system, and the MRI system may process the signals received from the RF coils via the connector in order to produce images of the body of the patient (e.g., images of the anatomical features of the patient to be imaged by the central RF coil array 312).

The neck RF coil assembly further includes a first peripheral RF coil array 302 that includes two rows of RF coils (first row 306 and second row 308) distributed along respective axes parallel to the central longitudinal axis at respective edges of a second substrate layer 304. First row 306 includes five RF coils and second row 308 includes five RF coils for a total of ten RF coils, but other numbers of RF coils are possible. First row 306 includes a first RF coil 310 that includes a loop portion 309 and a coupling electronics portion 311, similar to the RF coil 202 described above with respect to FIG. 2. Each RF coil of the first peripheral RF coil array 302 may be configured similarly (e.g., including a loop portion and a coupling electronics portion). Each loop portion of each RF coil of the first peripheral RF coil array 302 may have the same diameter. In an example, each diameter may be larger than the diameter of the RF coils of the central RF coil array 312, for example, the diameter may be 8 cm.

Each of the two rows of RF coils are coupled along a respective edge of the second substrate layer 304. For example, each RF coil of first row 306 may be coupled along a first edge of the second substrate layer 304 (e.g., a first long edge) and each RF coil of second row 308 may be coupled along a second edge of the second substrate layer (e.g., a second long edge). A center strip of the second substrate layer 304 may be free from RF coils loop portions. Each RF coil of the two rows may be coupled to the second substrate layer 304 only along a relatively small segment of the respective loop portions, thereby forming what is referred to herein as an "open loop" RF coil arrangement. For example, for a given loop portion, a segment that comprises 10-40% of the circumference of that loop portion may contact and/or be positioned over the second substrate layer 304, while the remaining segment of that loop portion (e.g., the remaining 60-90% of the loop portion) may be open to ambient, at least in some examples. Further, the RF coils may be distributed along the second substrate layer 304 in a non-overlapping manner so that none of the loop portions of the first row overlap with neighboring loop portions of the first row, and none of the loop portions of the second row overlap with neighboring loop portions of the second row. In this way, the loop portions may move independently of each other and partially independently of the second substrate layer 304. For example, each loop portion may flex/bend around a respective contact point where that loop portion contacts the substrate.

Additionally, a coil-interfacing cable 313 extends between each coupling electronics portion and an RF coil interfacing connector. Each of the electrical wires coupled to the coupling electronics portions may be housed together (e.g., bundled together) within the coil-interfacing cable 313 and electrically coupled to the connector. The connector may interface with the MRI system (e.g., electrically couple with the MRI system by plugging into an input of the MM system) in order to output signals from the RF coils to the MM system, and the MRI system may process the signals received from the RF coils via the connector in order to produce images of the body of the patient (e.g., images of the anatomical features of the patient to be imaged by the first peripheral RF coil array 302).

The neck RF coil assembly may further include a second peripheral RF coil array 320 that is configured similarly as the first peripheral RF coil array 302, including two rows of RF coils (e.g., first row 324 and second row 326) distributed along respective edges of a third substrate layer 322 in an open loop RF coil arrangement (e.g., such that only a small segment (e.g., 30% of a circumference) of each loop portion contacts/extends over the third substrate layer and the majority of each loop portion does not contact or extend over the third substrate layer). The second peripheral RF coil array 320 may include a greater number of RF coils than the first peripheral RF coil array 302 (e.g., 12 RF coils versus 10 RF coils). Each RF coil of the second peripheral RF coil array 320 may be configured similarly to the RF coil described above with respect to FIG. 2. For example, first row 324 includes an RF coil 328 comprised of a loop portion 327 and a coupling electronics portion 329. The second peripheral RF coil array 320 may include a coil interfacing cable 331 coupling each coupling electronics portion of the second peripheral RF coil array 320 to a connector, as explained above. In some examples, each coil interfacing cable of the neck RF coil assembly 400 may connect to a common connector that is configured to couple to a suitable port (which may be positioned on the table on which the subject to be imaged is positioned, such as table 26 of FIG. 1). In other examples, each coil-interfacing cable may connect to a separate connector, and each connector may couple to a respective (or the same) port on the MRI system (e.g., on the table).

FIG. 4 schematically shows the neck RF coil assembly 400 when the first peripheral RF coil array 302 and the second peripheral RF coil array 320 are stacked together and the central RF coil array 312 is stacked on top of the first and second peripheral RF coil arrays. The RF coils of the central RF coil array 312 may be facing outward, as shown (some detail, such as the coupling electronics parts and coil interfacing cables, have been removed from FIG. 4 for visual purposes). The center strips of the second and third substrate layers of the peripheral RF coil arrays may align and overlap with the first substrate layer 314 and the plurality of RF coils 316 of the central RF coil array. Both the first row 306 of the first peripheral RF coil array and the first row 324 of the second peripheral RF coil array may overlap each other and extend outward in a first direction from the overlapping substrate layers. The RF coils of the first row 306 and the first row 324 may be staggered relative to each other. For example, loop portion 327 and loop portion 309 may substantially overlap, with one half of loop portion 327 overlapping with one half of loop portion 309; the other half of loop portion 309 may overlap with the next loop portion of first row 324. Collectively, first row 306 and first row 324 may form an upper RF coil array 402 that extends outward from central RF coil array 312 and, in the example shown, comprises eleven staggered RF coils. The upper RF coil array 402 includes a plurality of overlapped RF coils that are coupled along a first (e.g., upper) edge of a substrate section, where the substrate section is comprised of the first substrate layer 314, the second substrate layer 304, and the third substrate layer 322. Each RF coil of the upper RF coil array 402 may contact and/or be co-extensive with the substrate section only along a small portion of the loop portion of that RF coil, and the remaining portion of the loop portion may not contact or be co-extensive with the substrate section.

Both the second row 308 of the first peripheral RF coil array and the second row 326 of the second peripheral RF coil array may overlap each other and extend outward in a second, opposite direction from the overlapping substrate layers. The RF coils of the second row 308 and the second row 326 may be staggered relative to each other. For example, each loop portion of second row 308 may overlap with part (e.g., half) of one loop portion of second row 326 and with part (e.g., half) of another loop portion of second row 326. Collectively, second row 308 and second row 326 may form a lower RF coil array 404 that extends outward from central RF coil array 312 and, in the example shown, comprises eleven staggered RF coils. The lower RF coil array 404 includes a plurality of overlapped RF coils that are coupled along a second (e.g., lower) edge of the substrate section. Each RF coil of the lower RF coil array 404 may contact and/or be co-extensive with the substrate section only along a small portion of the loop portion of that RF coil, and the remaining portion of the loop portion may not contact or be co-extensive with the substrate section.

As explained above, the RF coils of the central RF coil array 312 fully overlap with the first substrate layer (and hence the substrate section). As a result, the RF coils of the central RF coil array may be configured to bend or flex along with the substrate section at a plurality of axes that are perpendicular to the central longitudinal axis 406 of the neck RF coil assembly 400. For example, the central longitudinal axis 406 may be parallel to the Y axis of the coordinate system illustrated in FIG. 4, and the RF coils of the central RF coil array 312 may be configured to bend at a plurality of axes that are each parallel to the X axis of the coordinate system. However, due to the coupling of the RF coils of the central RF coil array 312 to the first substrate layer 314, the central RF coil array 312 may be constrained and may not bend (or bend less than the bending in the axes perpendicular to the central longitudinal axis) at the central longitudinal axis 406 or any other axes parallel to the Y axis. Likewise, the central RF coil array 312 may not bend (or bend more than a small amount) at axes parallel to the Z axis.

Figure 5:
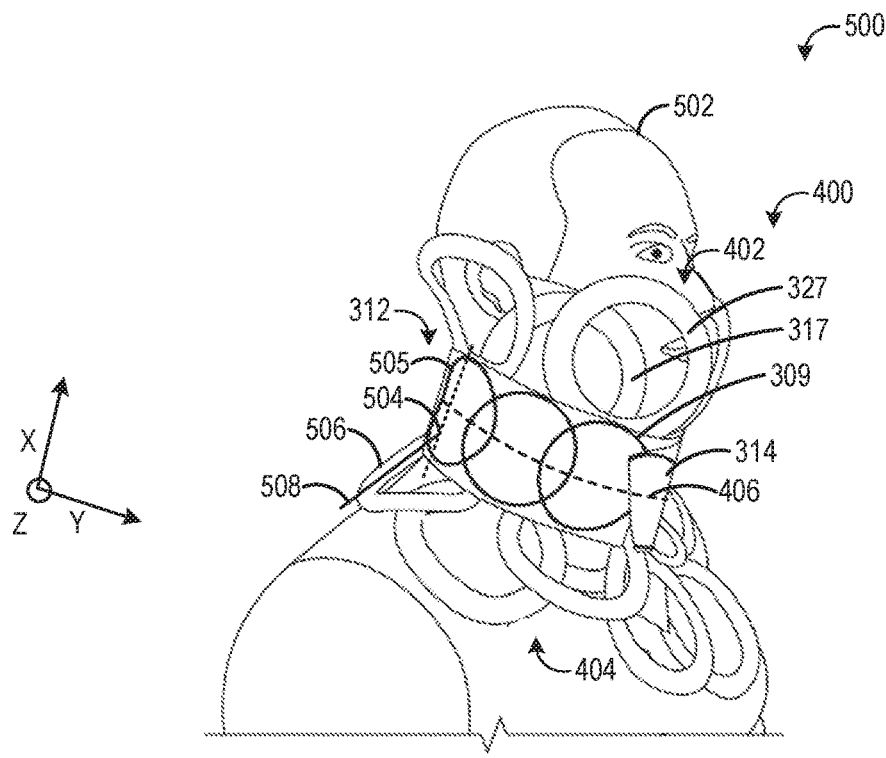
FIGS. 5 and 6 schematically show the first example RF coil assembly wrapped around the neck of an imaging subject.
Figure 6:
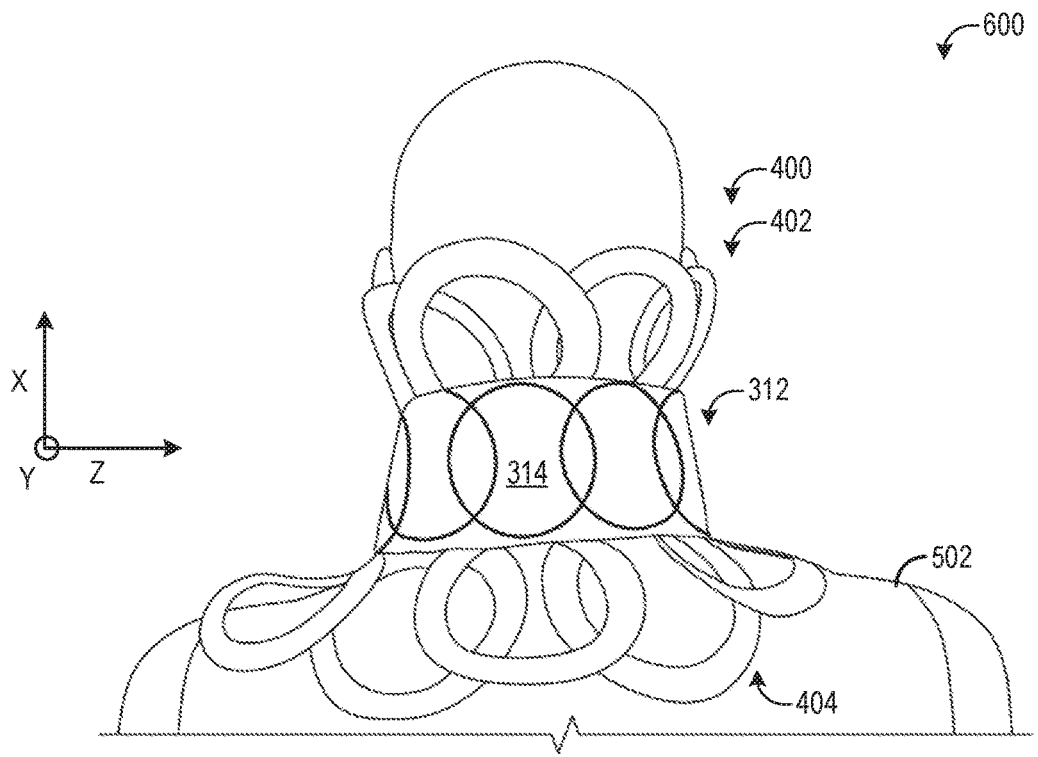

In contrast, the RF coils of the upper RF coil array 402 and the RF coils of the lower RF coil array 404 may only overlap with the substrate layers of the substrate section along a small segment of the respective loop portions of the RF coils. The remaining segments of the loop portions may not be constrained by the substrate section. Thus, the RF coils of the upper RF coil array 402 and the RF coils of the lower RF coil array 404 may bend and flex in multiple planes, and may bend and flex in more planes than the RF coils of the central RF coil array 312. For example, when the neck RF coil assembly is in a flat, first configuration, as shown in FIG. 4, the RF coils of the upper and lower RF coil arrays may extend along a first plane with the central RF coil array (such as the x-y plane shown in FIG. 4). When the neck RF coil assembly 400 is positioned in a second, imaging configuration, such as around a neck of a subject to be imaged (as shown in FIGS. 5 and 6 and explained in more detail below), the RF coils of the upper and lower RF coil arrays may bend or flex along with the substrate section to conform to the annular shape formed by the central RF coil array, and also may move out of a respective plane defined by the substrate section to accommodate the anatomical features/geometries of the body of the subject to be imaged. The RF coils may bend at respective contact points where the RF coils couple to a respective substrate layer and may be in a plane that is angled with respect to the respective plane defined by the substrate section. The RF coils may be configured to move into a range of angled planes where the range of angles is −90° to 90° or other suitable angle ranges. Each RF coil of the upper and lower RF coil arrays move independently of each other.

It should be understood that the first and second peripheral RF coil arrays and the central RF coil array are explained separately for the purpose of clarity. In some embodiments, at least two of the RF coils may be coupled to the same substrate (e.g., made of flexible fabric material).

For example, in some embodiments, the first and second peripheral RF coil arrays are coupled to the same substrate, overlapping with each other in the way as discussed above. In some embodiments, the first and second peripheral RF coil arrays are coupled to the same substrate to which the central RF coil array is attached, all coil arrays overlapping in the way as discussed above.

FIGS. 5 and 6 show the neck RF coil assembly 400 in the imaging configuration (e.g., being worn by a subject to be imaged, such as a patient or other human subject). FIG. 5 shows a side view 500 of a subject 502 wearing the neck RF coil assembly 400 and FIG. 6 shows a back view 600 of the subject 502 wearing the neck RF coil assembly 400. When the neck RF coil assembly 400 is wrapped around the subject's neck, the central RF coil array 312 may extend around and conform to the subject's neck. The central RF coil array 312 may bend along a plurality of axes to conform to an annular shape that matches the shape of the outer surface of the neck.

The upper RF coil array 402 may extend upward from the neck and toward the ears of the subject, wrapping around the chin/lower head region of the subject. The lower RF coil array 404 may extend downward from the neck and toward the chest/shoulders of the subject, wrapping around the lower neck/upper chest region of the subject. Due to the open loop arrangement of the RF coils of the upper and lower RF coil arrays, the RF coils of the upper and lower RF coil arrays may be bendable and are free to move to conform to the contours of the subject's neck, chin, face, chest, and so forth. The RF coils may include sufficient rigidity, however, to maintain the RF coils in close contact with the subject's body. As exemplified in FIG. 5, a tangent plane may be defined by the substrate section (e.g., first substrate layer 314) at an axis 504 tangent to the circle formed by the central RF coil array 312 and perpendicular to the central longitudinal axis 406. A loop portion of the central RF coil array 312 that intersects the axis 504 (loop portion 505) extends along with the substrate in the tangent plane. However, a loop portion of the lower RF coil array (loop portion 506) bends out of the tangent plane and is in a plane 508 that is angled relative to the tangent plane, such as angled outward in the negative z direction at an angle of 30° relative to the tangent plane. Loop portion 506 may bend along a contact point where loop portion 506 couples to the substrate section of assembly 400, such as at an edge of the first substrate layer 314 and/or where loop portion 506 couples to either the second substrate layer or third substrate layer (which may be positioned below first substrate layer 314 in FIG. 5 and thus are not visible).

As appreciated by FIGS. 5 and 6, each RF coil loop portion of the upper and lower RF coil arrays may bend at an appropriate angle to accommodate underlying patient anatomy, and each loop portion of the upper and lower RF coil arrays may move/bend/flex independently of the other loop portions of the upper and lower RF coil arrays. The loop portions of the RF coils of the central RF coil array, however, may be constrained by the substrate section and as such may be more flexible along axes perpendicular to the longitudinal axis (e.g., the short direction) than along axes parallel to the longitudinal axis (e.g., the long direction). For example, along a circumference of the substrate section formed when the neck RF coil assembly 400 is wrapped around the subject's neck, the RF coils of the central RF coil array may bend to conform to the annular shape of the substrate section, but at any plane defined by the substrate section, the RF coils of the central RF coil array may not bend out of the plane but may conform to the substrate section, which may not bend significantly in the long direction defined by the central longitudinal axis. The RF coils of the upper and lower RF coil arrays may likewise bend to conform to the annular shape, and may also bend out of any planes defined by the substrate section.

While FIGS. 5 and 6 show the plurality of RF coils of the central RF coil array 312 as being positioned on an outside of the assembly 400 when the assembly is worn by subject 502, in some examples the assembly 400 may be flipped so that the plurality of RF coils of the central RF coil assembly 312 are positioned on an inside of the assembly 400 and thus in contact (whether directly or indirectly via an overlaying substrate layer) with the neck of the subject 502. Further still, while each loop portion of the upper and lower RF coil arrays are shown as being uncovered (e.g., not covered by, coupled to, or in contact with a cover made of, for example, fabric material), in some examples one or more of the loop portions of the RF coils of the upper and/or lower RF coil arrays may be coupled to, covered by, or in contact with a cover, which may help to protect the RF coils and/or the imaging subject. The covers may be comprised of the same or different material than the substrate layers comprising the substrate section. The covers may cover one or both sides of the loop portions.

The substrate layers (e.g., first substrate layer 314, second substrate layer 304, and third substrate layer 322) may be formed of a flexible fabric material that is transparent to RF signals. In one example, the substrate layers of the neck RF coil assembly 400 may be formed of one or more layers of Nomex® material.

In this way, the neck RF coil assembly 400 may be configured to conform to the neck while also accommodating the flaring out of the subject anatomy away from the neck (e.g., toward the head and toward the chest). This flexible and conformable nature of the RF coil assembly is provided by the central RF coil array, which can be wrapped around the neck and is sized and shaped to match the neck. For example, the central RF coil array may include ten overlapping RF coils each with a diameter of six cm, which may provide for a total RF coil coverage of 50-60 cm (depending on the level of overlap) along the longitudinal axis, which may correspond to an average neck size. To accommodate subjects with different neck sizes, the ends of the central RF coil array may overlap when wrapped around the neck, and/or more or fewer RF coils may be included or the RF coils may be smaller or larger. The flexible and conformable nature of the assembly is further provided by the upper and lower RF coil arrays, which can bend independently of each other and semi-independently of the substrate section of the assembly. To accommodate the flaring nature of the anatomy, the upper and lower RF coil assemblies may each be comprised of RF coils that have a larger diameter than the RF coils of the central RF coil array, and at least in the example shown, may each include more RF coils than the central RF coil array. In this way, the upper and lower RF coil arrays may provide RF coil coverage over the head and chest regions, respectively, which may each have a larger diameter than the more narrow neck region.

FIG. 7 schematically shows an RF coil array 700 that may be included as part of a neck RF coil assembly in accordance with a second exemplary embodiment. RF coil array 700 includes a plurality of RF coils, and each RF coil is similar to RF coil 202 described above with respect to FIG. 2 (e.g., includes a loop portion and coupling electronics portion). The RF coil array 700 includes three sections: a head section (or upper section), a neck section (or central section), and a chest section (or lower section). Each section includes a plurality of RF coils arranged in a row, and each section partially overlaps with at least one other section. The head section is configured to wrap around a jaw/lower head region of a subject to be imaged (e.g., a patient or other human subject), the neck section is configured to wrap around a neck of the subject, and the chest region is configured to be positioned on an anterior upper chest region of the subject. Further, the RF coil array 700 optionally includes a chin coil configured to be positioned over a chin of the subject.

The head section of the RF coil array includes a first plurality of RF coils arranged in a row. As shown in FIG. 7, the head section includes four head RF coils and one chin RF coil, although the chin RF coil is optional. When included, the chin RF coil includes a loop portion 702 and coupling electronics portion 703. A first head RF coil includes a loop portion 704 and a coupling electronics portion 705, a second head RF coil includes a loop portion 706 and a coupling electronics portion 707, a third head RF coil includes a loop portion 708 and a coupling electronics portion 709, and a fourth head RF coil includes a loop portion 710 and a coupling electronics portion 711. The RF coils of the head section partially overlap with one another. For example, loop portion 704 partially overlaps with loop portion 706. When the chin RF coil is omitted, a gap without any RF coils may be present between loop portion 706 and loop portion 708. When included, loop portion 702 partially overlaps with loop portion 706 and loop portion 708. Loop portion 702 may have a larger diameter than the other loop portions in the head section, and the other loop portions in the head section may all have the same diameter.

The neck section of the RF coil array includes a second plurality of RF coils arranged in a row. As shown in FIG. 7, the neck section includes six neck RF coils. A first neck RF coil includes a loop portion 712 and a coupling electronics portion 713, a second neck RF coil includes a loop portion 714 and a coupling electronics portion 715, a third neck RF coil includes a loop portion 716 and a coupling electronics portion 717, a fourth neck RF coil includes a loop portion 718 and a coupling electronics portion 719, a fifth neck RF coil includes a loop portion 720 and a coupling electronics portion 721, and a sixth neck RF coil includes a loop portion 722 and a coupling electronics portion 723. The RF coils of the neck section partially overlap with one another. For example, loop portion 712 partially overlaps with loop portion 714. Further, each loop portion of the neck section overlaps with at least one loop portion of the head section. For example, loop portion 712 partially overlaps with loop portion 704, loop portion 714 partially overlaps with loop portion 704 and loop portion 706, and so forth. Each loop portion in the neck section may have the same diameter as the other loop portions in the neck section.

The chest section of the RF coil array includes a third plurality of RF coils arranged in a row. As shown in FIG. 7, the chest section includes five chest RF coils. A first chest RF coil includes a loop portion 724 and a coupling electronics portion 725, a second chest RF coil includes a loop portion 726 and a coupling electronics portion 727, a third chest RF coil includes a loop portion 728 and a coupling electronics portion 729, a fourth chest RF coil includes a loop portion 730 and a coupling electronics portion 731, and a fifth neck RF coil includes a loop portion 732 and a coupling electronics portion 733. The RF coils of the chest section partially overlap with one another. For example, loop portion 724 partially overlaps with loop portion 726. Further, each loop portion of the chest section overlaps with at least one loop portion of the neck section. For example, loop portion 724 partially overlaps with loop portion 712. Each loop portion in the chest section may have the same diameter as the other loop portions in the chest section.

Thus, the RF coil array 700 is arranged into three rows of RF coils in an overlapping manner (e.g., where the RF coils of a given row partially overlap with each other along the row, and where the RF coils of two adjacent rows partially overlap with each along an interface between the rows). Other than the chin RF coil, each other RF coil of the RF coil array 700 may be equal in size and may be spaced apart from neighboring RF coils by an equal amount. In this way, an equal and uniform amount of decoupling may be present between each RF coil. However, in other examples, different RF coils may have different sizes and/or may be spaced apart by different amounts. While not shown in FIG. 7, each RF coil of the RF coil array 700 is coupled to a coil interfacing cable that couples each coupling electronics portion to a connector, as explained above with respect to FIG. 3.

To facilitate close coupling of each RF coil of the RF coil array 700 around the complicated geometry of the head, neck, and chest region, the RF coil array 700 may be coupled to inner surfaces of a semi-rigid pillow. The semi-rigid pillow may be shaped similar to a neck pillow, and may include a chest region configured to cover an anterior region of a chest, a first side flap configured to extend from a lower face region (e.g., a cheek) around a first side of a neck, and a second side flap configured to extend from the lower face region (e.g., the other check) around a second side of the neck. The semi-rigid pillow may further include a neck region coupling the chest region to the first side flap and the second side flap, and in some examples, a chin flap. Each region/flap of the semi-rigid pillow may include at least one RF coil of the RF coil array 700. During imaging, the semi-rigid pillow may be placed over the anterior chest and neck of the subject, in a manner similar to a reverse neck pillow.

Figure 8:
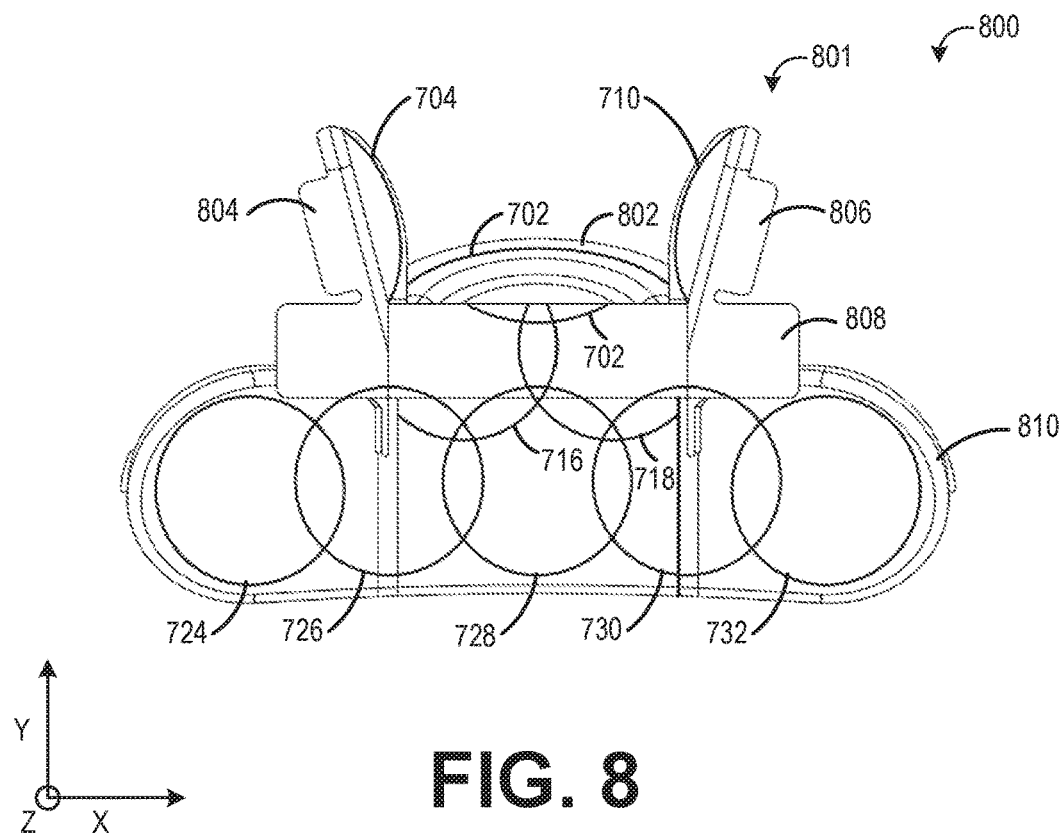
FIG. 8 shows a back view of the second example RF coil assembly including the RF coil array mounted on a semi-rigid pillow.
Figure 9:
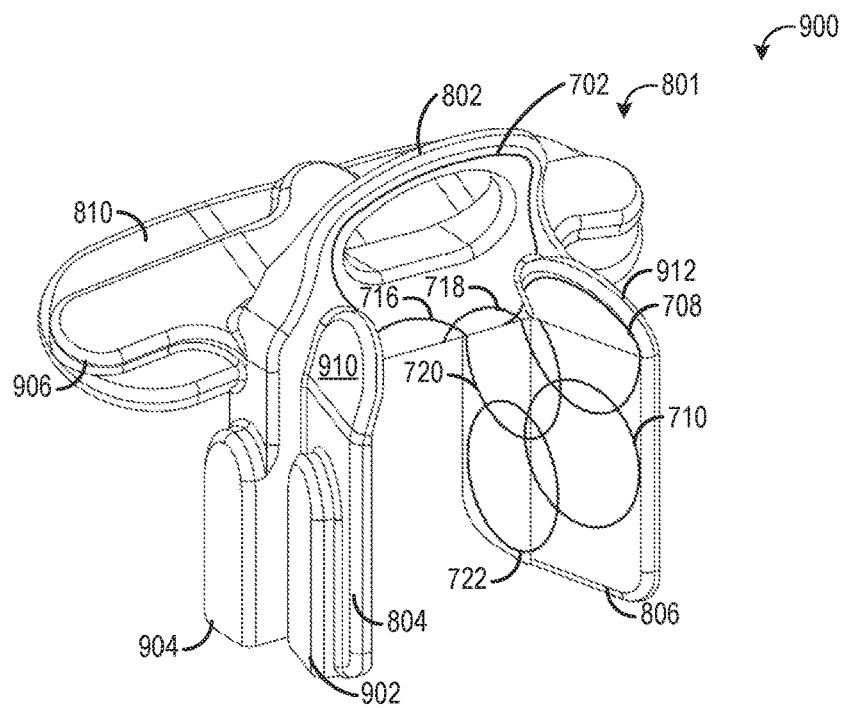
FIG. 9 shows a top isometric view of the second example RF coil assembly.
Figure 10:
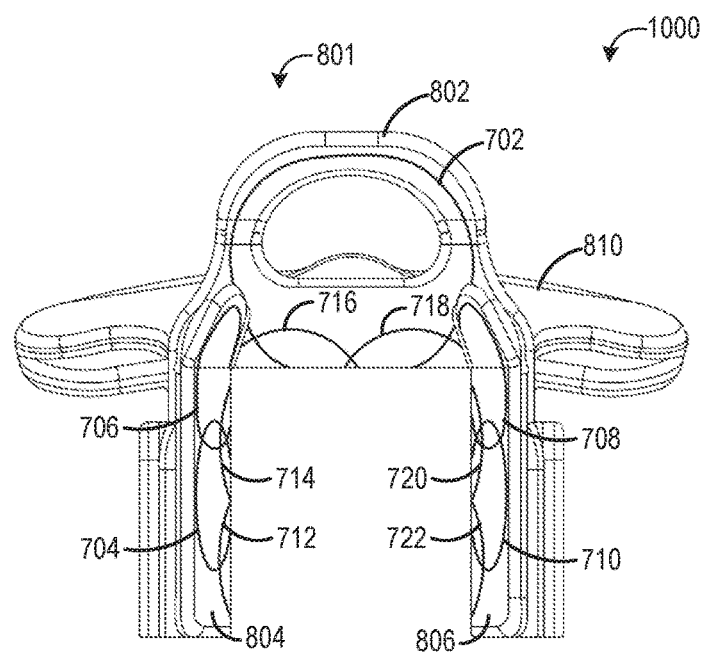
FIG. 10 shows a top down view of the second example RF coil assembly.

FIGS. 8-10 show various views of a neck RF coil assembly 801 that includes the RF coil array 700 coupled to a semi-rigid pillow. FIG. 8 is a back view 800 of the pillow, where inner surfaces of the chest region and neck region are visible. The semi-rigid pillow includes a chin flap 802, a first side flap 804, a second side flap 806, a neck region 808, and a chest region 810. Each region and flap of the semi-rigid pillow may be made of a conformable/flexible material such as foam. RF coil array 700 is distributed across inner surfaces of the semi-rigid pillow. For example, as shown in FIG. 8, the RF coils of the chest section are distributed across the chest region 810, such that loop portion 724, loop portion 726, loop portion 728, loop portion 730, and loop portion 732 are coupled to chest region 810. At least a portion of the RF coils of the neck section are coupled to neck region 808, such as loop portion 716 and loop portion 718, as shown in FIG. 8. The RF coils of the head portion are coupled across the two side flaps. For example, in FIG. 8, loop portion 704 is coupled to first side flap 804 and loop portion 710 is coupled to second side flap 806. Loop portion 702 is coupled to chin flap 802.

FIG. 9 shows a top isometric view 900 of the neck RF coil assembly 801. As illustrated in FIG. 9, each side flap includes RF coils of the head section and of the neck section of the RF coil array 700. For example, the second side flap 806 is coupled to loop portion 708 and loop portion 710 of the head section, and to loop portion 720 and loop portion 722 of the neck section. As shown in the top view 1000 of the neck RF coil assembly 801 shown in FIG. 10, the first side flap 804 is likewise be coupled to two RF coils of the head section (loop portion 704 and loop portion 706) and two RF coils of the neck section of the RF coil array 700 (loop portion 712 and loop portion 714). Further, FIGS. 9 and 10 show that two RF coils of the neck section (e.g., loop portion 716 and loop portion 718) are coupled to the neck region and extend/bend over onto the chin flap 802.

As shown in FIG. 9, the semi-rigid pillow includes a plurality of protrusions which may accommodate internal electronics of the RF coil array. For example, first side flap 804 includes a first protrusion 902 and a second protrusion 904. Chest region 810 includes a third protrusion 906, which may extend across an entirety of the chest region 810. While not shown in FIG. 9, the second side flap 806 may also include two protrusions similar to the first side flap 804. Additionally, some areas of the semi-rigid pillow may be angled relative to other regions in order to conform to underlying patient anatomy. For example, first side flap 804 includes a flex region 910 where the first side flap bends inward such that the flex region 910 is angled (e.g., at an angle of 10-30°) relative to the remaining portion of the first side flap 804. The second side flap 806 likewise includes a flex region 912 that bends inward relative to the rest of the second side flap. Loop portion 708 may bend to conform to the shape of the second side flap, such that loop portion 708 includes a first portion that is flat and aligned with a plane defined by the inner surface of the second side flap (e.g., a z-y plane) and a second portion that is angled inward relative to the first portion. Chin flap 802 may also bend inward, and loop portion 702 may bend to conform to the shape of the chin flap.

Figure 11:
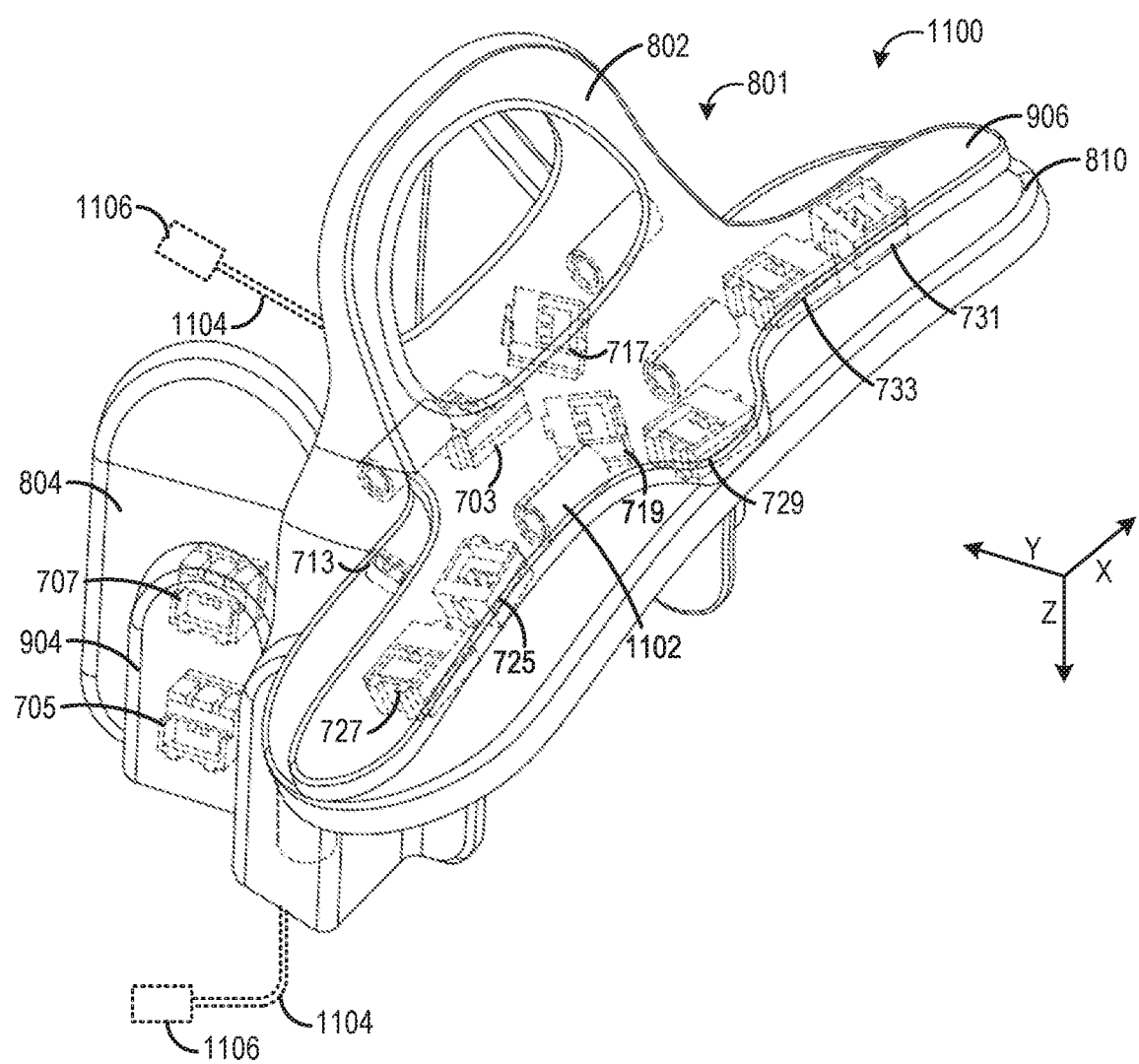
FIG. 11 shows a top isometric view of internal electronics of the second example RF coil assembly within the foam substrate.
Figure 13:
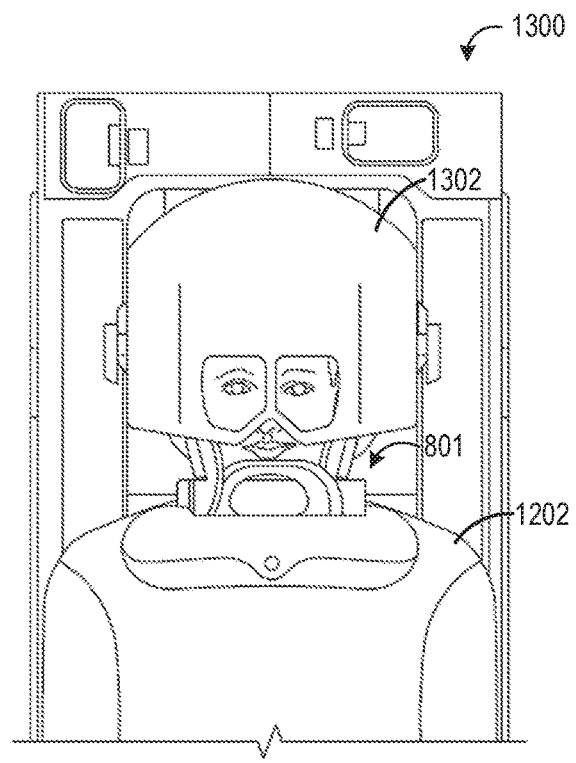
FIG. 13 shows the second example RF coil assembly and a head RF coil assembly on the imaging subject.

FIG. 11 shows another top isometric view 1100 of the neck RF coil assembly 801. In the view 1100, the semi-rigid pillow is made partially transparent so that inner electronics of the RF coil array 700 are visible. As shown, coupling electronics portion 707 and coupling electronics portion 705 of the head section of the RF coil array 700 are included in the first protrusion of the first side flap 804; the coupling electronics portions of the other RF coils of the head section are likewise included in the second side flap. A coupling electronics portion 713 of the neck section is also shown in the second protrusion of the first side flap 804. A coupling electronics portion of the neck section (coupling electronics portion 717) is shown as being included in the neck region 808 and/or chin flap 802, as well as coupling electronics portion 703. The coupling electronics portions of the chest section are included in the third protrusion of the chest region 810, including coupling electronics portion 727, coupling electronics portion 725, coupling electronics portion 729, coupling electronics portion 733, and coupling electronics portion 731. Further, coupling electronics portion 719 (which is part of an RF coil of the neck section) is also positioned in the chest region 810. Also included in the inner electronics is a plurality of baluns, such as balun 1102. Neck RF coil assembly 801 further includes a coil interfacing cable 1104 coupled to a connector 1106, similar to the coil interfacing cable and connector described above with respect to FIG. 3 (e.g., the coil interfacing cable may be coupled to each coupling electronics portion, and each balun shown in FIG. 11 may be included as part of the coil interfacing cable). The coil interfacing cable 1104 may exit the semi-rigid pillow at one of two possible locations. In a first embodiment, the coil interfacing cable 1104 may exit the semi-rigid pillow on a bottom of the first side flap 804 and connect to connector 1106, which may be configured to couple to a port on the table on which the subject to be imaged may be positioned (such as table 26 of FIG. 1). In some examples, as shown in FIG. 13 and explained below, the neck RF coil assembly 801 may be used in concert with a head RF coil configured to be placed around the head of the imaging subject. The head RF coil may be configured to connect to two ports on the table, and due to the number of channels in the head RF coil (e.g., 48), a plurality of channels (e.g., 16) of one of the ports on the table may be available. In such examples, connector 1106 may be configured to connect to the port on the table that may also be coupled to a portion of the channels of the head RF coil. In a second embodiment, the coil interfacing cable 1104 may exit the semi-rigid pillow near the top, on one (or in some examples, both) of the sides of the semi-rigid pillow, and couple to connector 1106. In the second embodiment, connector 1106 may be configured to couple to a port positioned in the head RF coil (shown in FIG. 13).

The semi-rigid pillow may be comprised of a suitable material that is transparent to RF signals and maintains desired rigidity while allowing some flexibility and conformability, such as polyurethane foam, polystyrene, nylon, or other suitable material. In some examples, the different regions and flaps described herein may be comprised of different pieces of material that are coupled together to form the semi-rigid pillow. When separate pieces of material are coupled together, the pieces may be coupled together using adhesive, thermal welding, or other non-rigid coupling mechanism, thereby avoiding the use of rigid joints, hinges, or other mechanisms. In other examples, two or more of the regions and/or flaps described herein may be comprised of a single piece of material. For example, the entire pillow may be made from one piece of material that is cut/shaped to form the final pillow. The internal electronics (e.g., coupling electronics portions, baluns, coil-interfacing cable) may be embedded within the material (e.g., embedded within the foam) and the loop portions may be coupled on surfaces of the material. The semi-rigid pillow may be covered in an outer cover to protect the internal components and maintain sterility, where the cover is thin and flexible (e.g., formed of a flexible material that is transparent to RF signals, such as one or more layers of Nomex® material or Nomex Nano® material). In still other examples, the semi-rigid pillow may be comprised of an outer substrate that is shaped as shown herein once filled with a filler material, where the filler material is comprised of discrete particles.

Figure 12:
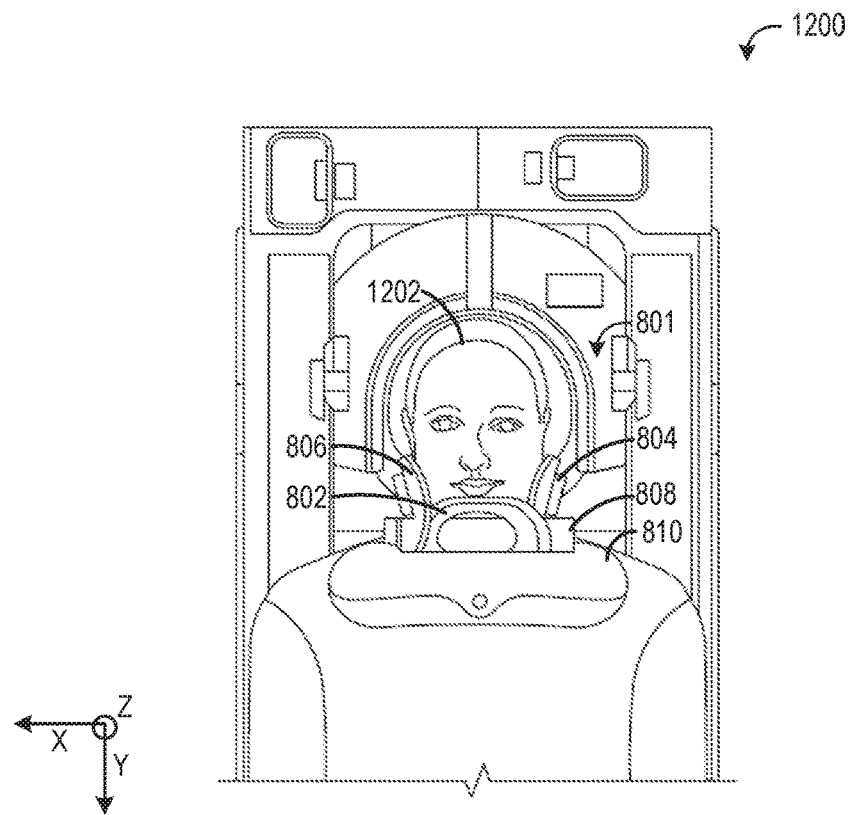
FIG. 12 shows the second example RF coil assembly on the neck and chest of an imaging subject.

FIGS. 12 and 13 show the neck RF coil assembly 801 positioned over a subject to be imaged. In a first view 1200 of FIG. 12, the neck RF coil assembly 801 is positioned over a subject 1202 that is lying on a table (in some examples, the table may include additional RF coils to image a posterior of the subject). The chest region 810 is positioned over an anterior upper chest of the subject, the first side flap 804 extends from a cheek of the patient around a side of the neck of the subject, the second side flap 806 extends from the other cheek of the patient around the other side of the neck of the subject, and the neck region 808 is positioned over the anterior part of the neck. The chin flap 802 extends upward from the neck region 808 and over the chin of the subject. As appreciated by second view 1300 of FIG. 13, the neck RF coil assembly 801 may be used together with a traditional head coil assembly, such as head coil assembly 1302, in order to image the entirety of the subject's head, neck, and cervical spine region.

A technical effect of the neck RF coil assemblies described herein is increased depth of imaging of the head, neck, and spine region.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A radio frequency (RF) coil assembly for a magnetic resonance imaging (MRI) system, comprising:
   a central RF coil array including a first plurality of RF coils configured to cover a neck of a subject to be imaged;
   an upper RF coil array including a second plurality of RF coils extending upward from the central RF coil array and configured to cover a lower head region of the subject; and
   a lower RF coil array including a third plurality of RF coils extending downward from the central RF coil array and configured to cover an upper shoulder region of the subject,
   wherein each RF coil of the first, second, and third pluralities of RF coils comprises a loop portion comprising two distributed capacitance wire conductors encapsulated and separated by a dielectric material;
   wherein:
   the first plurality of RF coils are distributed along a central longitudinal axis of a first substrate;
   the second plurality of RF coils comprises coils coupled along a first edge of a second substrate and coils coupled along a first edge of a third substrate;
   the third plurality of RF coils comprises coils coupled along a second edge of the second substrate and coils coupled along a second edge of the third substrate;
   wherein each RF coil of the second plurality of RF coils contacts the respective second or third substrate section only along a small portion of the loop portion of that RF coil, and a majority portion of the loop portion does not contact the respective second or third substrate section; and
   wherein the first substrate, the second substrate and the third substrate are stacked upon each other.

2. The RF coil assembly of claim 1, wherein each RF coil further comprises a coupling electronics portion for connecting to a data acquisition unit of the MM system, wherein the coupling electronics portion includes a decoupling circuit and an impedance inverter circuit.

3. The RF coil assembly of claim 1, wherein the RF coils of the first plurality of RF coils are distributed along the first substrate in an overlapping manner, wherein the RF coils of the second plurality of RF coils are distributed along the first edge of the second substrate and first edge of the third substrate in an overlapping manner, and the RF coils of the third plurality of RF coils are distributed along the second edge of the second substrate and the second edge of the third substrate in an overlapping manner.

4. The RF coil assembly of claim 1, further comprising a cover enclosing the central, upper, and lower RF coil arrays.

5. The RF coil assembly of claim 4, wherein the cover is made of a flexible fabric material.

6. The RF coil assembly of claim 1, wherein:
   when the RF coil assembly is in a first, flat configuration, the first substrate extends in a first plane and the first plurality of RF coils extend in the first plane, and
   when the RF coil assembly is in a second, imaging configuration, the first substrate forms an annular shape and the first plurality of RF coils bend at one or more axes to conform to the annular shape, and at any axis perpendicular to the central longitudinal axis, the first substrate defines a tangent plane at that axis and any RF coils of the first plurality of RF coils in that tangent plane extend along with the first substrate in that tangent plane.

7. The RF coil assembly of claim 6, wherein:
   when the RF coil assembly is in the first configuration, each RF coil of the upper RF coil array and the lower RF coil is configured to bend out of the first plane; and
   when the RF coil assembly is in the second configuration, the upper RF coil array and lower RF coil array each bend at the one or more axes to conform to the annular shape, and at any tangent plane, any RF coils of the upper RF coil array and the lower RF coil array are configured to bend out of the tangent plane.

8. The RF coil assembly of claim 1, wherein the central RF coil array comprises ten RF coils, the upper RF coil array comprises eleven RF coils, and the lower RF coil array comprises eleven RF coils.

9. The RF coil assembly of claim 1, wherein each loop portion of the first plurality of RF coils has a first diameter, each loop portion of the second plurality of RF coils has a second diameter, and each loop portion of the third plurality of RF coils has a third diameter, the second diameter and the third diameter being larger than the first diameter.

10. The RF coil assembly of claim 1, wherein the RF coils are coupled to the substrates using adhesive, thermal welding, or other non-rigid coupling mechanism.

11. The RF coil assembly of claim 1, wherein the stacked first substrate, the second substrate and the third substrate form a three-layer structure.

* * * * *